United States Patent [19]

Harris et al.

[11] Patent Number: 5,364,948
[45] Date of Patent: Nov. 15, 1994

[54] BIOLOGICALLY ACTIVE COMPOUNDS ISOLATED FROM AEROBIC FERMENTATION OF TRICHODERMA VIRIDE

[75] Inventors: Guy H. Harris, Cranford; Deborah Zink, Manalapan, both of N.J.; E. Tracy T. Jones, Solana Beach, Calif.; Yu L. Kong, Edison, N.J.

[73] Assignee: Merck & Co., Inc., Rahway, N.J.

[21] Appl. No.: 15,498

[22] Filed: Feb. 9, 1993

Related U.S. Application Data

[63] Continuation-in-part of Ser. No. 739,758, Aug. 2, 1991, abandoned, and a continuation-in-part of Ser. No. 907,730, Jul. 9, 1992, abandoned.

[51] Int. Cl.$^5$ .................................. C07C 233/00
[52] U.S. Cl. ............................... 554/36; 554/35; 554/61; 554/63; 554/213; 554/218; 554/227; 554/228; 554/229; 548/469; 548/534
[58] Field of Search ............... 424/404; 554/213, 218, 554/227, 228, 229, 36, 61, 63; 548/469, 534

[56] References Cited

U.S. PATENT DOCUMENTS

| | | | |
|---|---|---|---|
| 4,231,938 | 11/1980 | Monaghan et al. | 260/343 |
| 4,254,273 | 3/1981 | Powell et al. | 560/29 |
| 4,535,176 | 8/1985 | Natarajan et al. | 560/27 |
| 4,673,690 | 6/1987 | Roberfroid et al. | 514/563 |
| 4,871,721 | 10/1989 | Biller | 514/102 |
| 5,026,554 | 6/1991 | Bartizal et al. | 424/404 |
| 5,053,425 | 10/1991 | Bartizal et al. | 514/452 |
| 5,055,487 | 10/1991 | Bartizal et al. | 514/452 |
| 5,096,923 | 3/1992 | Bergstrom et al. | 514/452 |
| 5,102,907 | 4/1992 | Bergstrom et al. | 514/456 |
| 5,135,935 | 8/1992 | Alberts et al. | 514/305 |

FOREIGN PATENT DOCUMENTS

| | | |
|---|---|---|
| 512865 | 5/1982 | European Pat. Off. |
| 375133 | 11/1989 | European Pat. Off. |
| 475706 | 9/1991 | European Pat. Off. |

OTHER PUBLICATIONS

M. J. Dawson et al., Journal of Antibiotics, vol. 45(5): pp. 639–647 (1992).

Database WPIL/Derwent Publ., AN 84-272218 c44! & JP59166094 (1984).

A. A. Qureshi et al., The Independent Roles Of Genetic And Dietary Factors In Determining The Cholesterol Status Of Laying Hens[1], Nutrition Reports International, vol. 34 No. 3, pp. 457–464, (1986).

*Primary Examiner*—José G. Dees
*Assistant Examiner*—Deborah D. Carr
*Attorney, Agent, or Firm*—Catherine A. Dolan; Melvin Winokur; Paul D. Matukaitis

[57] ABSTRACT

This invention relates to compounds of structural formula (I) isolated from an aerobic fermentation of *Trichoderma viride* MF5628, ATCC 74084:

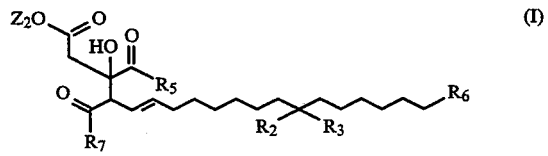

(I)

which are squalene synthase inhibitors and thus useful as cholesterol lowering agents. These compounds are also potent antifungal agents. Additionally, they inhibit farnesyl protein transferase and farnesylation of the oncogene protein Ras and are thus useful in treating cancer. This invention also relates to a process for obtaining compounds of structural formula (I).

11 Claims, No Drawings

BIOLOGICALLY ACTIVE COMPOUNDS ISOLATED FROM AEROBIC FERMENTATION OF TRICHODERMA VIRIDE

CROSS-REFERENCE TO RELATED APPLICATION

This application is a continuation-in-part of U.S. Application Ser. Nos. 07/739,758 filed Aug. 2, 1991 and 07/907,730 filed Jul. 9, 1992, both abandoned.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin) and ZOCOR® (simvastatin), now commercially available, are members of a group of very active antihypercholesterolemic agents that function by limiting cholesterol biosynthesis by inhibiting the enzyme HMG-CoA reductase.

Squalene synthase (also called squalene synthetase) is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthase have employed pyrophosphate or pyrophosphate analog containing compounds such as those described in P. Ortiz de Montellano et al., J. Med. Chem. 20, 243 (1977), E. J. Corey and R. Volante, J. Am. Chem. Soc., 98, 1291 (1976), and U.S. Pat. No. 5,025,003 to S. Billet. U.S. Pat. No. 4,871,721 to S. Billet describes isoprenoid(phosphinylmethyl) phosphonates as inhibitors of squalene synthase.

U.S. Pat. Nos. 5,096,923; 5,026,554; and 5,102,907 and U.S. patent applications Ser. Nos. 496,734 filed Mar. 21, 1990, and 698,766 filed May 10, 1991 disclose non-phosphorus-containing substituted 2,8-dioxabicyclo[3.2.-1]octane derivatives useful as squalene synthase inhibitors. Furthermore, J. Antibiotics 45: 639–658 (1992) describe a squalene synthase inhibitor called squalestatin.

Recently it has been shown that certain natural product nonphosphorous containing inhibitors of squalene synthase and their esters are useful in inhibiting fungal growth. This utility is described in U.S. Pat No. 5,026,554.

The present invention is directed to the use of compounds of structural formula (I) which are squalene synthase inhibitors for the inhibition of fungal growth.

The present invention is also directed to the use of compounds of structural formula (I) which are inhibitors of farnesyl protein transferase for inhibition of farnesylation of the oncogene protein Ras and the treatment of cancer.

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., Mi-crobiol. Rev. 53:171–286 (1989)). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., Nature 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., Cell 57:1167 (1989); Casey et al., Proc. Natl. Acad. Sci. USA 86:8323 (1989)). In addition, Ha-Ras and N-Ras are palmitoylated via formation of a thioester on a Cys residue near a C-terminal Cys farnesyl acceptor (Gutierrez et al., EMBO J. 8:1093–1098 (1989); Hancock et al., Cell 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., J. Biol. Chem. 263:18236 (1988); Farnsworth et al., J. Biol. Chem. 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci. USA, 87:7541–7545 (1990)).

Inhibition of farnesyl-protein transferase and, thereby, of farnesylation of the Ras protein, blocks the ability of Ras to transform normal cells to cancer cells. Surprisingly, the compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., Proc. Natl. Acad. Sci. USA 86:6630–6634 (1989)). Cytosol-localized forms of Ras with normal GTPase activity do not act as inhibitors. Gibbs et al., ibid, showed this effect in Xenopus octyes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist.

In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

These compounds are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects then is the case for a general inhibitor of isoprene biosynthesis.

Previously, it has been demonstrated that tetrapeptides with the CAAX sequence inhibit Ras farnesylation (Schaber et al., ibid: Reiss et. al., ibid; Reiss et al., *PNAS*, 88:732–736 (1991)). However, the reported inhibitors of farnesyl-transferase are metabolically unstable or inactive in cells.

Pharmaceutical compositions containing the compounds of this invention and methods of treatment utilizing these compositions for use in inhibiting farnesyl-protein transferase and farnesylation of the oncogene protein Ras are described herein.

DETAILED DESCRIPTION OF THE INVENTION

The present invention is directed to novel compounds of structural formula (I) which are squalene synthase inhibitors, antihypercholesterolemic agents, antifungal agents, and anticancer agents:

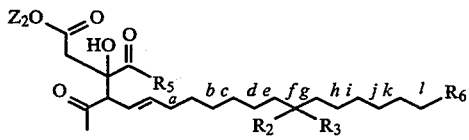

wherein
$R_1$ is:

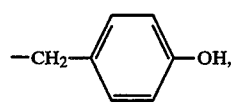

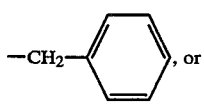

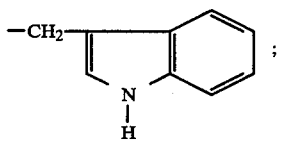

$R_2$ and $R_3$ are each H, or $R_2$ is H and $R_3$ is OH, or $R_2$ and $R_3$ together are oxo;

$R_4$ is H and $R_5$ is $OZ_3$, or $R_4$ and $R_5$ together are a bond to the nitrogen, forming a 2,5-dioxopyrrolidine ring;

$R_6$ is
(a) hydrogen, or
(b) $C_{1-3}$ alkyl;

$R_7$ is:
(a) $-OZ_1$, or

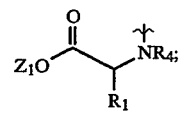

each of a, b, c, d, e, f, g, h, i, j, k, and l are a single bond or one of a, b, c, d, e, f, g, h, i, j, k, and l is a double bond, provided that when f or g is a double bond, $R_2$ is absent and $R_3$ is H; and $Z_1$, $Z_2$ and $Z_3$ are independently:
a) H,
b) $C_{1-5}$alkyl, or
c) $C_{1-5}$alkyl substituted with
   i) phenyl, or
   ii) phenyl substituted with methyl, methoxy, halogen (Cl, Br, F, I) or hydroxy;

or a pharmaceutically acceptable salt of a compound of formula (I).

In one class of compounds of this invention, a, b, c, d, e, f, g, h, i, j, k, and l each are a single bond, and $R_7$ is $-N(R_4)CH(R_1)C(=O)OZ_1$.

One sub-class of this first class of compounds are those in which $R_1$ is p-hydroxybenzyl, $R_2$ and $R_3$ are together oxo, $R_4$ is hydrogen, $R_5$ is $OZ_3$, and $R_6$ is methyl. Exemplifying this sub-class are those compounds wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as Compound A.

Further illustrating this sub-class are those compounds in which $R_1$ is p-hydroxybenzyl and $R_2$ and $R_3$ are together oxo, $R_4$ is hydrogen and $R_5$ is $OZ_3$, $R_6$ is methyl and in which one or more of $Z_1$, $Z_2$ or $Z_3$ is $C_{1-5}$alkyl or $C_{1-5}$alkyl substituted with phenyl or substituted phenyl wherein the substituent is methyl, methoxy, halogen or hydroxy. In a specific illustration, $Z_1$, $Z_2$ and $Z_3$ are each methyl. This compound is hereafter referred to as Compound B. In another specific illustration, $Z_2$ is methyl and $Z_1$ and $z_3$ are hydrogen. This compound is Compound I. In yet another specific illustration, $Z_1$ is methyl and $Z_2$ and $Z_3$ are each hydrogen. This compound is Compound J. The compound wherein $Z_1$ and $Z_2$ are each methyl and $Z_3$ is hydrogen is Compound K.

Another subclass are those compounds in which $R_1$ is benzyl, $R_2$ and $R_3$ are together oxo, $R_4$ is hydrogen, $R_5$ is $OZ_3$ and $R_6$ is methyl. Exemplifying this subclass are those compounds wherein $Z_1$, $Z_2$ and $Z_3$ are each hydrogen or a pharmaceutically acceptable salt thereof. The compound wherein $R_1$ is benzyl, $R_2$ and $R_3$ are together oxo, $R_4$ is hydrogen, $R_5$ is $OZ_3$, $R_6$ is methyl and $Z_1$, $Z_2$ and $Z_3$ are each hydrogen is hereafter referred to as Compound C. Further illustrating this subclass are those compounds in which one or more of $Z_1$, $Z_2$ or $Z_3$ is $C_{1-5}$ alkyl or $C_{1-5}$ alkyl substituted with phenyl or substituted phenyl wherein the substituent is methyl, methoxy, halogen or hydroxy.

A third subclass are those compounds in which $R_1$ is —$CH_2$—3-indolyl and $R_2$ and $R_3$ are together oxo, $R_4$ is hydrogen, $R_5$ is $OZ_3$, and $R_6$ is methyl. Exemplifying this subclass are those compounds wherein $Z_1$, $Z_2$, and $Z_3$ are each hydrogen or a pharmaceutically acceptable salt thereof. The compound wherein $Z_1$, $Z_2$ and $Z_3$ are each hydrogen is hereafter referred to as Compound D. Further illustrating this subclass are those compounds in which one or more of $Z_1$, $Z_2$ or $Z_3$ is $C_{1-5}$ alkyl or $C_{1-5}$ alkyl substituted with phenyl or substituted phenyl wherein the substituent is methyl, methoxy, halogen or hydroxy.

A fourth subclass are those compounds in which $R_1$ is —$CH_2$—3-indolyl and $R_2$ is H, $R_3$ is hydroxyl, $R_4$ is hydrogen, $R_5$ is $OZ_3$, and $R_6$ is methyl. Exemplifying this subclass are the compounds wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as Compound F. Further illustrating this subclass are those compounds in which one or more of $Z_1$, $Z_2$ or $Z_3$ is $C_{1-5}$ alkyl or $C_{1-5}$ alkyl substituted with phenyl or substituted phenyl wherein the substituent is methyl, methoxy, halogen or hydroxy.

A fifth subclass are those compounds in which $R_1$ is p-hydroxybenzyl, $R_2$ and $R_3$ together are oxo, $R_4$ is hydrogen, $R_5$ is $OZ_3$ and $R_6$ is n-propyl. Exemplifying this subclass are those compounds wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as Compound G. Further illustrating this subclass are those compounds in which $R_1$ is p-hydroxybenzyl and $R_2$ and $R_3$ are together oxo, $R_4$ is hydrogen, $R_5$ is $OZ_3$, $R_6$ is n-propyl, and in which one or more of $Z_1$, $Z_2$ and $Z_3$ is $C_{1-5}$ alkyl or $C_{1-5}$ alkyl substituted with phenyl or substituted phenyl wherein the substituent is methyl, methoxy, halogen or hydroxy.

In a sixth subclass are those compounds wherein $R_1$ is p-hydroxybenzyl, $R_2$ and $R_3$ are together oxo, $R_4$ and $R_5$ are together a single bond and $R_6$ is methyl. Exemplifying this subclass are those compounds wherein $Z_1$ and $Z_2$ are each hydrogen or a pharmaceutically acceptable salt thereof. The compound of this subclass wherein $Z_1$ and $Z_2$ are each hydrogen is hereafter referred to as Compound H. Further illustrating this subclass are those compounds in which one or both of $Z_1$ and $Z_2$ is $C_{1-5}$ alkyl or $C_{1-5}$ alkyl substituted with phenyl or substituted phenyl wherein the substituent is methyl, methoxy, halogen or hydroxy.

In a seventh subclass are those compounds wherein $R_1$ is p-hydroxybenzyl, $R_2$ and $R_3$ are each hydrogen, $R_5$ is —$OZ_3$ and $R_6$ is methyl. Exemplifying this subclass are those compounds wherein $Z_1$, $Z_2$ and $Z_3$ are each hydrogen or a pharmaceutically acceptable salt thereof. The compound of this subclass wherein $Z_1$, $Z_2$ and $Z_3$ are each hydrogen is hereafter referred to as Compound E. Further illustrating this subclass are those compounds in which one or more of $Z_1$, $Z_2$ and $Z_3$ is $C_{1-5}$ alkyl or substituted $C_{1-5}$ alkyl substituted with phenyl or substituted phenyl wherein the substituent is methyl, methoxy, halogen or hydroxy.

Additional compounds of the first class of compounds of this invention wherein $Z_1$ is OH, $Z_2$ is OH, $Z_3$ is OH, $R_4$ is H, $R_5$ is OH, and $R_1$, $R_2$, $R_3$, and $R_6$ are as listed in Table 1 below:

TABLE 1

| Compound | $R_1$ | $R_2$ | $R_3$ | $R_6$ |
|---|---|---|---|---|
| L | benzyl | —H | —H | —$CH_3$ |
| M | benzyl | oxo with $R_3$ | oxo with $R_2$ | —$CH_2CH_2CH_3$ |
| N | p-hydroxybenzyl | —H | —OH | —$CH_3$ |
| O | p-hydroxybenzyl | oxo with $R_3$ | oxo with $R_2$ | —H |
| R | benzyl | oxo with $R_3$ | oxo with $R_2$ | —H |
| S | benzyl | —H | —OH | —$CH_3$ |

In a second class of compounds of this invention, $R_7$ is —$N(R_4)CH(R_1)C(=O)OZ_1$, and one of a, b, c, d, e, f, g, h, i, j, k, and l is a double bond provided that when f or g is a double bond, $R_2$ is absent.

One sub-class of this second class of compounds are those in which $R_1$ is benzyl, $R_2$ and $R_3$ are each H, $R_4$ is hydrogen, $R_5$ is $OZ_3$, and $R_6$ is methyl. Exemplifying this sub-class are those compounds wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as Compound Q. Further illustrating this sub-class are those compounds in which one or more of $Z_1$, $Z_2$ or $Z_3$ is $C_{1-5}$alkyl or $C_{1-5}$alkyl substituted with phenyl or substituted phenyl wherein the substituent is methyl, methoxy, halogen or hydroxy.

Another subclass are those compounds in which $R_1$ is p-hydroxybenzyl, $R_2$ and $R_3$ are together oxo, $R_4$ is hydrogen, $R_5$ is —$OZ_3$ and $R_6$ is methyl. Exemplifying this subclass are those compounds wherein $Z_1$, $Z_2$ and $Z_3$ are each hydrogen or a pharmaceutically acceptable salt thereof. The compound of this second class wherein $R_1$ is p-hydroxybenzyl, $R_2$ and $R_3$ are together oxo, $R_4$ is hydrogen, $R_5$ is $OZ_3$, $R_6$ is methyl and $Z_1$, $Z_2$ and $Z_3$ are each hydrogen is hereafter referred to as Compound P. Further illustrating this subclass are those compounds in which $R_1$ is benzyl and in which one or more of $Z_1$, $Z_2$ or $Z_3$ is $C_{1-5}$ alkyl or $C_{1-5}$ alkyl substituted with phenyl or substituted phenyl wherein the substituent is methyl, methoxy, halogen or hydroxy.

In a third class of compounds of the present invention, $R_7$ is —$OZ_1$. In one particular subclass of this third class of the invention, $R_2$ and $R_3$ are both H, $R_5$ is —$OZ_3$, $R_6$ is methyl. The compound in this subclass wherein $Z_1$, $Z_2$ and $Z_3$ are each hydrogen and each of a, b, c, d, e, f, g, h, i, j, k, and l are a single bond is hereafter referred to as Compound T.

The compounds of formula (I) are prepared in an aerobic fermentation procedure employing a novel fungal culture, MF5628, identified as *Trichoderma viride* Pers. or a mutant thereof. A mutant refers to an organism in which some gene on the genome is modified, leaving functional and heritable the gene or genes responsible for the organism's ability to produce the compounds of formula (I) in recoverable amounts. *Trichoderma viride* is a common and geographically widespread organism, present in many soils and organic substrata throughout the world.

The culture MF5628 is that of a fungus, *Trichoderma viride* Pers., isolated from soil collected in Kolonia, Pohnpei (formerly Ascension Island), Federated States of Micronesia. This culture has been deposited with the American Type Culture Collection at 12301 Parklawn Drive, Rockville, Md. 20852 as ATCC 74084 on Jul. 30, 1991, under the conditions of the Budapest Treaty.

Within the genus Trichoderma, this strain can be assigned to *Trichoderma viride* species aggregate (Rifai, M. A. 1969. A revision of the genus Trichoderma. CMI Mycological Paper 116: 1–56) because it lacks sterile terminal appendages on the conidiophores, the phialides are long, tapered and arranged in a regular, dendritic pattern, and the conidia are, for the most part, subglobose and roughened.

The culture MF5628, identified as *Trichoderma viride* exhibits the following morphological features.

Colonies growing rapidly on most standard mycological media. On corn meal agar, malt-extract agar, or oatmeal agar reaching 40–45 mm in 48 hours at 27° C. and covering a 9 cm plate in about five days. At first, colonies on malt-extract agar hyaline to white, sparse to loosely floccose, at maturity becoming dark yellowish green to dark green because of conidial production, Dark Green, Dark Yellowish Green, reverse olive yellow to Light Yellowish Olive (capitalized color names from Ridgway,R.,1912. *Color Standards and Nomenclature,* Washington, D.C.). On corn meal agar, tufts of conidiophores forming concentric rings, alternating with zones of hyaline, hyphae, on maltextract and oatmeal agars, conidiophores develop uniformly over the agar surface.

Mycelium hyaline, septate, smooth-walled, 2.6–3.8 $\mu$m wide, forming chlamydospores which are globose to subglobose, smooth, 5.7–9.5 $\mu$m diameter. Conidiophores arising from surface of colony, often aggregated in pulvinate conidial pustules, profusely branched at wide angles, either singly or in groups of two or three in opposite or whorled arrangement, with branches decreasing in length towards the apex, terminating with phialides. Conidiogenous cells enteroblastic, phialidic, narrowly flask-shaped, slender, tapered at the apices, 5.7–9.5×2 $\mu$m, straight or slightly curved, single, or in groups of two or three, at wide angles to the conidiophore branch, forming a regular dendritic pattern, never together in dense aggregations. Conidia subglobose to ovoid 3.0–4.5×2.6–3.0 $\mu$m, pale green in KOH, slightly toughened, accumulating as a cluster at tips of the phialides.

Compounds of this invention can be obtained by culturing the above-noted microorganism in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (eg. ammonium nitrate, ammonium sulfate, ammonium phosphate, etc.) can also be used. The various sources of nitrogen can be used alone or in combination in amounts ranging between 0.2 to 70 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic conditions.

Compounds of formula (I) may be isolated from the aerobic fermentation of a culture of MF5628 (ATCC 74084). A culture of MF5628 (ATCC 74084) is defined as substantially free of its natural soil contaminants and capable of forming compounds of structural formula (I) in recoverable amounts. A biologically pure culture of MF5628 (ATCC 74084) may also be employed. A biologically pure culture is substantially free from viable deleterious contaminating microorganisms.

The fermentation procedure generally is to first inoculate a preserved source of culture into a nutrient seed medium and to obtain, sometimes through a two-step process, growth of the organisms which serve as seeds in the production of the active compounds. After inoculation, the flasks are incubated with agitation at temperatures ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 6 to 22 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24 to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound isolated.

An alcoholic or oxygenated solvent such as an ester or ketone, preferably MEK is stirred with the solid fermentation, and the MEK extract is collected by vacuum filtration. The solids remaining can be extracted and the extracts combined and concentrated in vacuo. The concentrated extract is dissolved in a pH 4.5 buffer, preferably 60 parts acetonitrile to 40 parts 50 mM sodium formate pH 4.5. The solution is extracted with a highly hydrophobic solvent such as hexanes to yield a defatted extract. The defatted aqeuous extract is purified by anion exchange chromatography preferably BIORAD AG4X4 (formate cycle), washing with the aqueous buffer and eluting. Fractions containing the mixture of the compounds of the invention are pooled, diluted with water and extracted into an organic solvent such as ethyl acetate. The extract is washed, dried and concentrated in vacuo.

Further purification is accomplished using reversed-phase high pressure liquid chromatography (RP-HPLC). The preferred adsorbent for this chromatography is a octadecylsilane bonded phase silica gel. The preferred eluant for RP-HPLC is a mixture of acetonitrile and water buffered at low pH, such as 0.1% phosphoric or trifluoroacetic acid.

Further purification may also be accomplished using high speed countercurrent chromatography. The preferred solvent system is a mixture of hexanes: ethyl acetate: methanol: 0.1% aqueous phosphoric acid (5:5:5:5). The preferred apparatus is the ITO multilayer-coil manufactured by P.C. Inc., Potomac, Md. U.S.A.; however, other countercurrent chromatography equipment may be used.

Esters of Compounds A, C, D, E, F, G, H, I, J, K, L, M, N, O, P, Q, R, S and T may be prepared by dissolving a compound selected from Compound A, C, D, E, F, G, H, I, J, K, L, M, N, O, P, Q, R, S, and T in a dry organic solvent, preferably tetrahydrofuran (THF) at 0°-30° C. and treating with the appropriately substituted isourea for 8-24 hours, cooling to $-15°$ C. and filtering the urea. The mono-, di- and tri- esters of Compounds A, C, D, E, F, G, H I, J, K, L, M, N, O, P, Q, R, S and T may be prepared by varying the number of equivalents of isourea used. The filtrate is concentrated under reduced pressure to yield the desired ester.

The present invention is also directed to a method of inhibiting cholesterol biosynthesis which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

In addition, the present invention is directed to a method of inhibiting the enzyme squalene synthase which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form. These salts may be prepared by standard procedures.

The compounds of this invention may also be administered in combination with other cholesterol-lowering agents such as those which inhibit another enzyme in the biosynthetic pathway in the synthesis of cholesterol. Examples of such agents would include but are not limited to HMG-CoA reductase inhibitors, HMG-CoA synthase inhibitors, and squalene epoxidase inhibitors. Illustrative of such HMG-CoA reductase inhibitors are lovastatin, simvastatin, pravastatin and fluvastatin. Examples of RMG-CoA synthase inhibitors are the beta-lactone derivatives disclosed in U.S. Pat. Nos. 4,806,564; 4,816,477; 4,847,271; and 4,751,237; the beta-lactam derivatives disclosed in U.S. Pat. No. 4,983,597 and U.S. Ser. No. 07/540,992 filed Jun. 20, 1990; and the substituted oxacyclopropane analogues disclosed in European Patent Publication EP 0 411 703. Illustrative examples of squalene epoxidase inhibitors are disclosed in European Patent Publication EP 0 318 860 and in Japanese Patent Publication 302 169-571A. LDL-receptor gene inducer molecules are disclosed in U.S. patent application Ser. No. 07/670,640 filed Mar. 18, 1991. Other cholesterol lowering agents that may be administered include niacin, probucol, the fibtic acids: clofibrate and gemfibrozil, and LDL-receptor gene inducers. Representative of such combinations are those containing about 10-400 mg of a compound of formula (I) in combination with about 20-100 mg of an HMG-CoA reductase inhibitor, 20 to 200 mg of a HMG-CoA synthase inhibitor, or 1 to 200 mg of a squalene epoxidase inhibitor, or 250-1000 mg of probucol, or 600-1200 mg of gemfibrozil, or 1-2 g of clofibrate, or 3-6 g of niacin, or 20-300 mg of an LDL-receptor gene inducer.

The compounds of this invention may also be co-administered with pharmaceutically acceptable non-toxic cationic polymers capable of binding bile acids in a non-resorbable form in the gastrointestinal tract. Examples of such polymers include cholestyramine, colestipol and poly[methyl-(3-trimethyl)aminopropyl]iminotrimethylene dihalide. The relative amounts for co-administration of the compounds of this invention and these polymers is between 1:100 and 1:15,000 (w/w).

The intrinsic squalene synthase inhibitory activity of representative compounds of this invention was measured by the standard in vitro protocol described below:

PREPARATION OF HUMAN HepG2 CELL ENZYME

1. SOURCE: HEPG2 CELL LINE (Liver, hepatoblastoma, Human) ATCC No. HB 8065
2. CELL GROWTH AND MAINTENANCE Culture Medium: Minimum essential medium (MEM) with non-essential amino acids, sodium pyruvate, and 10% fetal bovine serum. The medium was changed twice weekly. A confluent monolayer was achieved in 1 week. The growth medium was prepared as listed below.

| | Solution | Volume (mL) |
|---|---|---|
| 1 | MEM (Gibco #320-1090AK) With Earle's salts and L-glutamine | 1000 |
| 2. | Penicillin (10,000 units/mL), streptomycin (10,000 mg/mL), Gibco #600-5140 PG | 10 |
| 3. | MEM sodium pyruvate, 10 mM (100X) Gibco #320-1140 | 10 |
| 4. | MEM nonessential amino acids, 10 mM (100X) Gibco #320-1140AG | 10 |
| 5. | L-glutamine, 200 mM (100X), Gibco #320-5030AG | 10 |
| 6. | Hyclone fetal bovine serum, defined, Hyclone #A-111-L | 100 |

SUBCULTURE PROCEDURE: The medium was removed and washed with PBS (Phosphate-Buffered Saline 15.6 mM, pH 7.0). Fresh trypsin (0.25%)-EDTA (0.02%) with Hank's Balanced Salt solution was added and the flask was allowed to stand for a minute before the trypsin solution was removed. The flask was incubated at 37° C. until cells detached. Fresh medium was added and the cells were dispersed and dispensed into new flasks. Subcultivation ratio: 1:6.

PREPARATION OF DELIPIDATED SERUM: Fetal calf serum (100 mL) and CAB-O-SIL (2 grams) were stirred overnight at 4° C. and centrifuged at 16,000 rpm for 5 h. The supernatant was filtered and the serum was stored at 4° C.

48 h prior to harvest, cells grown in MEM with 10% Fetal Calf serum were switched to MEM with 10% delipidated serum.

HARVEST: The medium was removed and the cells were washed with PBS. Fresh trypsin (0.25%)-EDTA (0.02%) with Hanks' Balanced Salt solution was added and allowed to stand and removed. The flask was incubated at 37° C. until the cells detached. MEM medium (6 mL/flask) was added to suspend cells and combined into a centrifuge tube. The cells were spun at 1,000 rpm for 5 mins. The cell pellet was resuspended in PBS and recentrifuged. Cells were counted ($2.5 \times 10^9$ yield from 18 flasks (75 cm$^2$)), and resuspended in 10 mL of 50mM HEPES (N-[2-Hydroxyethyl]piperazine-N'-[2-ethanesulfonic acid]) containing 5mM MgCl$_2$, 2mM MnCl$_2$, 10mM DTT, pH 7.5 (enzyme suspension buffer).

CELL EXTRACTS: The cell suspension was sonicated (probe sonicator setting #60, pulse) on ice for 2 min. After a 1 min. cooling on ice, the sonication was repeated until greater than 90% of the cells were broken as observed microscopically. The supernatant was centrifuged for 10 mins. at 10,000 rpm and the supernantant was transferred to a clean tube and centrifuged at 20,000 rpm for 20 mins. The HepG2 enzyme preparation was centrifuged at 34,000 rpm to separate the cytosol and microsomal enzymes. The resulting pellet from the 34,000 rpm centrifugation, containing the squalene synthase, was resuspended in 5 mL of enzyme suspension buffer. The enzyme suspension was diluted and used to perform the squalene synthase assay using 3μM $^3$H-farnesyl pyrophosphate as the substrate.

Preparation of Yeast Enzyme

*S. cerevisiae* W303-1A (MATa ade2-1 can1-100 his3-11,15 leu2-3,112 trp1-1 ura3-1) was grown at 30° C. for 24 hours in YPD medium (2% yeast extract, 1% bactopeptone, 2% glucose) supplemented with 20 μg/mL adenine. The cells were washed and resuspended in a minimal volume of breakage buffer (100 mM KPO$_4$, pH 7.4, 3 mM DTT, 1 mM PMSF). The cells were added to the small chamber of the Bead-Beater Cell Disrupter (Biospec Products, Bartlesville, Okla.) containing 100 g of 0.5 mm glass beads. Buffer was added to fill the chamber. The sealed chamber was packed in ice and processed for 4 cycles of 30 sec with 2 min. cooling between cycles. Cell breakage was determined to be >90% by phase-contrast microscopy. The glass beads were removed by Whatman filter paper and the filtrate collected into an ice-immersed filter flask. The extract was centrifuged at 1500 x g for 10 min at 4° C. The pellet (P1) containing unbroken cells and cell walls was discarded. The supernatant (S1) was centrifuged at 30000 x g for 30 min at 4° C. The pellet (P2) contained about two-thirds of the total squalene synthase activity. The supernatant (S2) can be centrifuged at 100,000 x g for 60 min at 4° C. to pellet the remaining activity (P3). The pellet fractions were suspended at 10–20 mg/ml protein in breakage buffer containing 25% glycerol. The activity was stable for several months at −80° C.

Squalene Synthase Assay

Reactions were performed in 1.2 mL polypropylene tube strips of eight. The standard reaction mixture in a total volume of 0.140 mL, contained HEPES-Na+ buffer pH 7.5 50 mM, NADPH 1 mM, MgCl$_2$ 5.5 mM, KF 11 mM, DTT 3 mM, terbinafine (Yeast squalene epoxidase inhibitor, Sandoz SF86-327) or mammalian squalene epoxidase inhibitor (Banyu FW-439H) 1 μg/mL, farnesyl pyrophosphate (FPP) 5μM (NEN), $^3$H-farnesyl pyrophosphate 0.25 μCi (NEN, 20 Ci/mmole), enzyme preparation 0.1 μg yeast protein or 0.4 μg HepG2 protein and test sample in 5 μl DMSO. All assays components except FPP/$^3$H-FPP were preincubated for 12 min at 30° C. to allow inhibitor to bind to the enzyme. The reactions were started with FPP/$^3$H-FPP addition. After 12 min at 30° C., the reactions were stopped by addition of 0.2 mL ethanol. The reaction product was extracted with 0.4 mL heptane containing 0.4 μL carrier squalene 0.2 mL of the heptane extract was counted by liquid scintillation. The IC$_{50}$ was determined as the concentration of inhibitor which gave 50% of the control (no inhibitor) enzyme activity as determined from a logarithmic curve fit of the data from a drug titration.

Percent inhibition is calculated by the formula:

$$\frac{(\text{Control} - \text{Sample}) \times 100}{\text{Control} - \text{Blank}}$$

IC$_{50}$ values were determined by plotting the log of the concentration of the test compound versus the percentage inhibition. The IC$_{50}$ is the concentration of inhibitor that gives 50% inhibition as determined from these plots.

Below are IC$_{50}$'s representative of the inherent squalene synthase inhibitory activity of the compound of the present invention.

| | Squalene Synthase Inhibition IC$_{50}$ (μg/mL) | |
|---|---|---|
| Compound | Yeast Enzyme | HepG2 Enzyme |
| Compound A | 7.5 | 41.6 |
| Compound C | 1 | 19.3 |
| Compound D | 0.22 | 0.29 |

Alternatively, the intrinsic squalene synthase inhibitory activity of the compounds formed in the fermentation of the microorganisms of the present invention may be measured by the standard in vitro protocol described below:

Preparation of Rat Liver Microsomes

Male, CHARLES RIVER ® CD rats (120 to 150 g) were fed a diet containing 0.1% lovastatin for 4 days. The livers from these rats were homogenized in 5 volumes (mL/g) of ice cold 50 mM HEPES (4-(2-hydroxyethyl)-1-piperazine-ethanesulfonic acid), 5 mM EDTA(ethylenediaminetetraacetic acid) pH 7.5 with a Potter-Elvehjem type tissue grinder. The homogenate was centrifuged twice at 20,000 x g for 15 min. at 4° C., discarding the pellet each time. The supernatant was then centrifuged at 100,000 x g for 1 hr at 4° C. The resulting microsomal pellet was resuspended in a volume of the above homogenizing buffer equal to one-fifth the volume of the original homogenate. This microsomal preparation has a protein concentration of about 7 mg/mL. The microsomal suspensions were stored in aliquots at −70° C. Squalene synthase activity in these aliquots is stable for a least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110, 125–129 (1985)) and a unit of activity is defined as the amount of enzyme that will produce 1 μmole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 mM leupeptin, 0,005% phenylmethylsulfonyl fluoride, pH 7.0 containing 0.1 trypsin inhibitor units of aprotinin/mL. The homogenate was centrifuged at 20,000 x g for 20 min. The supernatant was adjusted to pH 5.5. with 6 N HOAc and centrifuged at 100,000 x g for 1 hour. This supernatant was adjusted to pH 7.0 with 3 N KOH and a 35–60% ammonium sulfate fraction taken. The 60% pellet was redissolved in 60 mL of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4B equilibrated with Buffer A. The column was washed with 700 mL of Buffer A and a 1 liter gradient from Buffer A to 100 mM potassium phosphate, 10 mM mercaptoethanol, 1 mM EDTA, pH 7.0. Fractions having a specific activity greater than 0.20 units/mg were combined, solid ammonium sulfate was added to bring to 60% saturation and pelleted. The pellet was dissolved in 8 mL 10 mM Tris, 10 mM β-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/mL with specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for a least 6 months.

Enzymatic Synthesis of [4-$^{14}$C]farnesyl-pyrophosphate

The solvent (ethanol: 0.15 N NH$_4$OH, 1:1) was removed from 55 mCi of [4-$^{14}$C]isopentenyl pyrophosphate(47.9 mCi/mmole) by rotary evaporation. Six hundred microliters of 100 mM Tris, 10 mM MgCl$_2$, 4 mM dithiothreitol pH 7.5 was added and the solution was transferred to a 1.5 mL Eppendorf centrifuge tube. Geranyl-pyrophosphate, 250 mL of a 20 mM solution, and 50 mL of the ammonium sulfate suspension of prenyl transferase were added to initiate the reaction. This incubation contained 5 mmoles of geranyl pyrophosphate, 1.15 mmoles of isopentenyl pyrophosphate, 6 mmoles of MgCl$_2$ of 0.18 units of prenyl transferase in a volume of 900 mL. The incubation was conducted at 37° C. During the incubation, the mix turned cloudy white as the newly formed magnesium complex of farnesyl pyrophosphate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 mL of 50 mM HEPES, 5 mM EDTA, pH 7.5. The yield was 50.7 mCi (92%) of [4-$^{14}$C]farnesyl pyrophosphate. The [4-$^{14}$C]farnesyl pyrophosphate was stored in aliquots at −70° C.

Squalene Synthase Assay

Reactions were performed in 16×125 mm screw cap test tubes. A batch assay mix was prepared from the following solution:

| | mL per assay |
|---|---|
| 1. 250 mM HEPES pH 7.5 | 20 |
| 2. NaF 110 mM | 10 |
| 3. MgCl$_2$ 55 mM | 10 |
| 4. Dithiothreitol 30 mM | 10 |
| 5. NADPH 10 mM (made fresh) | 10 |
| 6. [4-$^{14}$C]farnesyl-pyrophosphate 47.9 mCi/mmole, and 0.025 mCi/3.0 mL | 3.0 |
| 7. H$_2$O | 24 |

This assay mix was degassed under a vacuum and flushed with N$_2$. Solutions of the squalene synthase inhibitors were prepared either in DMSO or MeOH and a 1:120 dilution of the microsomal protein was made with the original homogenizing buffer. For each reaction, 87 mL of the assay mix was taken with 3 mL of an inhibitor solution DMSO or MeOH in the controls), warmed to 30° C. in a water bath and then the reaction was initiated by the addition of 10 mL of the 1:120 dilution of microsomal protein (0.6 mg protein total in the assay). The reactions were stopped after 20 minutes by the addition of 100 mL of a 1:1 mix of 40% KOH with 95% EtOH. The stopped mix was heated at 65° C. for 30 min., and cooled. Ten mL of heptane was added and the mix was vortexed. Two g of activated alumina was then added, the mix vortexed again, the alumina allowed to settle and 5 mL of the heptane layer was removed. Ten mL of scintillation fluid was added to the heptane solution and radioactivity was determined by liquid scintillation counting.

Percent inhibition is calculated by the formula:

$$1 - \frac{[\text{Sample} - \text{Blank}]}{[\text{Control} - \text{Blank}]} \times 100$$

Representative of the squalene synthetase inhibitory character of the compounds of this invention is the datum below.

| Compound | Squalene Synthase IC$_{50}$ |
|---|---|
| Compound A | 15 μM |

The present compounds also demonstrate broad spectrum antifungal activity as determined by broth dilution methods. The compounds are particularly active towards filamentous fungi and yeasts including *Candida albicans* and *Ustilago zeae*. The sensitivity of filamentous fungi and yeast was determined using inhibitor dilution assays in microtiter format. The compounds were dissolved in DMSO at 2 mg/mL and diluted in 100 μL of DMSO. Exponential phase Candida, Cryptococcua and Ustilago cells were diluted in fresh YNB/G (Difco Yeast Nitrogen Base supplemented with 2% glucose) and YCB/Glu (Difco yeast carbon base with 2 mM 1-glutamic acid) such that the inoculum was $1 \times 10^4$ cells/mL. Aspergillus spores were harvested from a well-sporulated Sabouraud Dextrose Agar slant in 0.4% Tween 80 and diluted into media to give an inoculum of $1 \times 10^3$ spores/mL. The wells were filled with 150 μL of inoculated media. The final drug concentration tested ranged from 40 to 0.313 μg/mL. The microtiter dishes were incubated at 29° C. for 20 to 48 hours. The minimum inhibitory concentration (MIC) is defined as the lowest concentration to prevent visible growth after incubation for 20 hours at 29° C. for the yeasts and 24 to 48 hours at 29° C. for the filamentous fungi. Representative of the antifungal activity are the minimum inhibitory concentration data shown below.

| | Minimum Inhibitory Concentration (mg/mL) | | | |
|---|---|---|---|---|
| | | COMPOUND | | |
| Organism | Medium | A | C | D |
| *Candida albicans* MY1055 | YNB/G YCB/Glu | 40 5 | >40 2.5 | >40 20 |
| *Cryptococcus neoformans* MY2061 | YNB/G YCB/Glu | 40 1.25 | >40 1.25 | 40 10 |
| *Cryptococcus neoformans* MY2062 | YNB/G YCB/Glu | >40 2.5 | >40 5 | >40 10 |
| *Ustilago zeae* MF1996 | YNB/G YCB/Glu | 5 1.25 | 10 2.5 | 20 2.5 |
| *Aspergillus fumigatus* MF4839 | YNB/G YNB/Glu | >40 0.625 | >40 0.625 | >40 1.25 |

Thus the present invention is also directed to a method of inhibiting fungal growth which comprises the application to the area in which growth is to be controlled an antifungally effective amount of a compound of Formula (I). Additionally, the present invention is directed to a method of treating fungal infections which comprises the administration to an organism in need of such treatment a nontoxic therapeutically effective amount of a compound represented by the structural formula (I) and pharmaceutically acceptable salts thereof. Based on the above MIC data it is determined that generally from 2 to about 20 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such as lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium, the compositions may be applied directly to the plant in topical application or administered to the soil for systemic application. The method comprises administering to the affected plant, soil or medium to be protected an antifungally effective amount of the compound of Formula I.

The compounds of Formula I also exhibit Farnesyl-transferase inhibition, as shown below:

FARNESYL-TRANSFERASE ASSAY

I. PREPARATION OF SOLUTIONS REQUIRED FOR THE ASSAY i. 1.0 M $MgCl_2$ (MW=203.3)

203.3 g $MgCl_2$ was dissolved in 1.0 L distilled water, and filtered through a sterile filter and stored at 4° C.

ii. 1.1 M HEPES (MW=238.3) and 55.5 mM $MgCl_2$ 264.5 g of HEPES was added to 700 mL distilled water followed by 56 mL of 1.0 M $MgCl_2$. The pH was adjusted to 7.5 with sodium hydroxide and the volume was brought to 1000 mL. The solution was filtered through a sterile filter and stored at 4° C.

iii. 0.5 M Dithiothreitol (DTT, MW=154.24)

77.12 mg of DTT was dissolved in 1.0 mL of distilled water. A few drops of 10 N NaOH was added to get the DTT to go into solution. 0.5 M DTT was divided into 500 μL aliquots and stored at −20° C.

iv. Preparation of Assay Buffer (Prepare fresh daily)

100 μL of 0.5 M DTT was added to 900 μL of 1.1 M HEPES, pH 7.5 and 55.5 mM $MgCl_2$ to yield a 10X buffer consisting of 1.0 M HEPES, pH 7.5, 50 mM $MgCl_2$ and 50 mM DTT.

v. Preparation of unlabelled farnesyl pyrophosphate (FPP)

The unlabelled FPP (MW=433.3) was provided as a 1.8 mM (1 mg/1.28 mL) solution. This solution was diluted to 2 μM with water and prepared fresh weekly and stored at −20° C. Glass tubes were used when preparing the unlabelled FPP.

vi. Preparation of $^3$H-FPP

The $^3$H-FPP (NEN #NET-1042, MW=433.3) was used directly from the bottle as provided by NEN. The stock concentration of the $^3$H-FPP was 25 μM.

vii. Preparation of the reaction mix for Totals and unknown samples (on ice)

The reaction mix was prepared as below:

| Reagent | Stock Conc. | Vol to use/assay | Conc. in 20 μL | Final Conc. in assay |
|---|---|---|---|---|
| $^3$H-FPP | 25 μM | 0.2 μL | 0.25 μM | 50 μM |
| Cold-FPP | 2000 μM | 11.25 μL | 1.125 μM | 225 μM |
| ras-CVLS | 1 mg/ml (47.62 μM) | 6.3 μL | 15 μM | 3 μM |
| d-$H_2O$ | | 2.25 μL | | |
| TOTAL VOLUME | | 20 μL | | |

A Blank reaction mix was also prepared with the negative control ras-protein, and the Total/Sample reaction mix received the ras-CVLS. The same volumes were used to prepare the Blank reaction mix as those in Table 1.

viii. Preparation of the Farnesyl Transferase solution

The farnesyl trasferase solution was prepared as shown below. The farnesyl transferase mix was prepared right before use.

| Reagent | Stock Conc, | Vol to use/assay |
|---|---|---|
| d-$H_2O$ | | 14.0 μL |
| Buffer | stock = 10X | 10.0 μL |
| F. Transferase | stock = 1 mg/mL | 1.0 μL |

| Reagent | Stock Conc, | Vol to use/assay |
|---|---|---|
| Total Volume | | 25 μL | ix. Preparation of 1.0 M HCl in 100% Ethanol

The stop solution was prepared by mixing 43 mL of concentrated HCl (11.6 M) with 457 mL of 100% ethanol to yield 1.0 M HCl in ethanol.

v. STEPS FOR THE ASSAY i. The assay volume was 100 μL, the volume of sample to be tested was 5 μL and the time of incubation is 60 min at room temperature.

ii. The TECAN 8000/505, an automatic pipetting station, added 50 μL of water plus 5 μL of sample to the assay tubes.

iii. The ras-CVLS reaction mix (20 μL) was manually added to totals and unknowns. The negative control ras-protein reaction mix (20 μL) was manually added to the blank tubes.

iv. The farnesyl transferase mix (25 μL) was manually added to all tubes to initiate the reaction and the assay tubes were kept at room temperature for 60 min.

v. The assay was stopped placing the assay tubes in an ice bath for 5 minutes.

vi. 1.0 mL of 1.0 M HCl in 100% ethanol was then added to each tube. The assay tubes (uncapped) were incubated at 37° C. for 60 min. to facilitate the hydrolysis of the FPP.

vii. Assay tubes were harvested through a TOMTEC 96-well harvestor (6×16 with extended tips, or SKATRON cell harvestor) onto LKB double thickness filter mats.

viii. The cell harvester was adjusted so that each well was washed with 10 mL of 100% ethanol.

ix. Filter mats were baked in microwave oven for 6–8 min. to dry the filtermats.

x. The filter mats were placed in counting bags, 30 mL of LFB β-scint cocktail was added and the filter mats were counted for 120 sec. in the LKB β-plate counter.

VI. RESULTS AND DISCUSSION

Percent inhibition was calculated according to the following equation:

$$\% \text{ Inhibition} = \frac{[\text{Total} - \text{Sample}] \times 100}{[\text{Total} - \text{Blank}]}$$

The Farnesyl Transferase data presented below is a measurement of the ability of the test compound to inhibit Ras farnesylation in vitro.

| Compound | $IC_{50}$ (μM) |
|---|---|
| Compound A | 8 |
| Compound C | 4.5 |
| Compound D | 3.3 |

The pharmaceutical compositions containing the compounds of structural formula (I) inhibit farnesyl-protein transferase and the farnesylation of the onco-gene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone, or preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitioneal, subcutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in a amount between about 0.1 mg/kg of body weight to about 20 mg/kg of body weight of a mammal per day, preferably of between 0.5 mg/kg of body weight to about 10 mg/kg of body weight of a mammal per day.

The following examples illustrate the preparation of the compounds of formula (I) and their incorporation into pharmaceutical compositions and, as such, are not to be considered as limiting the invention set forth in the claims appended hereto.

The composition of media employed in the following Examples are listed below:

| KF SEED MEDIUM | per liter | Trace Element Mix #2 | g/L |
| --- | --- | --- | --- |
| Corn Steep Liquor | 5 g | FeSO$_4$.7H$_2$O | 1.0 |
| Tomato Paste | 40 g | MnSO$_4$.4H$_2$O | 1.0 |
| Oat Flour | 10 g | CuCl$_2$.2H$_2$O | 0.025 |
| Cerelose | 10 g | CaCl$_2$.2H$_2$O | 0.1 |
| Trace Element | | H$_3$BO$_3$ | 0.056 |
| Mix #2 | 10 mL | (NH$_4$)$_6$Mo$_7$O$_{24}$.4H$_2$O | 0.019 |
| Distilled Water | 1000 mL | ZnSO$_4$.7H$_2$O | 0.2 |
| pH adjusted to 6.8 (presterile) | | dissolved in 1L 0.6 N HCl | |
| 50 mL/non-baffled Erlenmeyer flask autoclave 20 minutes (121° C., 15 psi) | 250 mL | | |

Solid Substrate Production Medium

Solid substrate media prepared in nonbaffled 250 mL Erlenmeyer flasks
BRF: Brown rice 5.0 g/flask
Base liquid #3 20.0 mL/flask

| Base liguid #3 | g/L |
| --- | --- |
| Yeast extract | 1.0 |
| Sodium tartrate | 0.5 |
| KH$_2$PO$_4$ | 0.5 |
| distilled water | 1000.0 mL |

(no pH adjustment)
autoclave 15 minutes ( 121 ° C., 15 psi )
add 15.0 mL distilled water per flask
autoclave 20 minutes ( 121 ° C., 15 psi )

EXAMPLE 1

Preparation of Compound A

A. Culturing MF5628

Culture MF5628 was inoculated into 3 KF seed medium flasks using a mixture of hyphae and spores preserved in sterile soil. The KF seed flasks were incubated for 74 hours at 25° C., 220 rpm, 85% humidity. At the end of this incubation, culture growth from the 3 seed flasks was pooled and then 2.0 mL aliquots were aseptically transferred to each of 50 BRF solid production medium flasks. These production flasks were then incubated statically at 25° C., 85% humidity for 21 days. At harvest 50 mL methyl ethyl ketone (MEK) was added to each BRF production flask and the solid growth was manually broken apart into smaller pieces. Solvent treated flasks were returned to the gyrotory shaker for agitation at 220 rpm for 30 minutes in order to further break apart the mycelial mass as well as to improve contact of the solvent with the cells. After shaking, the contents of these flasks were pooled by pouring the entire contents of the flasks (solids and all) into a 2L flask.

B. Isolation of Compound A

The 21-day 2000 mL solid fermentation in BRF media from above was extracted with 2500 mL of methyl ethyl ketone (MEK) by stirring an additional 1.5 hours at room temperature. The extracted fermentation was then filtered through CELITE ®.

A portion of the MEK extract (300 mL) was concentrated to dryness in vacuo. The resulting residue was partitioned between 50 mL hexanes and 50 mL methanol. The methanol layer was concentrated to dryness in vacuo. The residue was dissolved in 100 mL of 1:1MeOH:100 mM NaOAc pH 4.8 and again extracted with 50 mL hexanes. The aqueous methanol layer was then loaded at 150 mL/hour onto a column of BioRad AG4-X4(acetate) (vol.=28ml,25mm×50 mm, 100-200 mesh) which had been equilibrated with 1:1 MeOH:100 mM NaOAc pH 4.8 (equilibration buffer). The column was then washed with 100 mL of equilibration buffer and then with 100 mL of 6:4 acetonitrile ($CH_3CN$):$H_2O$. The column was eluted with 0.16 N sulfuric acid in 6:4 $CH_3CN$:$H_2O$ collecting 8 mL fractions. Fractions 21 to 30 (6.0-8,6 column volumes) contained crude Compound A and were pooled (vol.=100 ml, pH 2.54) and extracted with 100 mL of ethyl acetate. The ethyl acetate layer was concentrated in vacuo to yield 384 mg crude Compound A which was dissolved in 20 mL methanol.

A portion (5.2 mL, 100mg) of the crude Compound A in methanol was concentrated to dryness in vacuo and dissolved in 1 mL of HPLC mobile phase. This solution was chromatographed on Whatman Partisil 10 ODS 3 (22 mm×25 cm) using 45% $CH_3CN$/55% $H_2O$ containing 0.1% $H_3PO_4$ at 20ml/min. The column was monitored at 220 nm and 0.4 min (8 ml) fractions were collected. Compound A eluted in fractions 44-49. Analytical HPLC (Partisil 5 ODS 3, 4.6 mm×25 cm, 55% $CH_3CN$/$H_2O$ containing 0.1% $H_3PO_4$, 1.0 mL min, detection at 220 nm) showed fractions 44 to 49 to contain essentially pure Compound A, $t_r$=4.25'. Fractions 44 to 49 were pooled and extracted with an equal volume (48 ml) of $CH_2Cl_2$, the $CH_2Cl_2$ layer removed, dried over anhydrous $Na_2SO_4$ and concentrated in vacuo to yield 20.6 mg pure Compound A.

EXAMPLE 2

Preparation of Compound C

A. Culturing MF 5628

Culture MF 5628 was grown according to the procedures of Example 1, Step A.

B. Isolation of Compound

A 1500 mL portion of the MEK extract from Example 1 Part B was processed through BioRad AG4x4 as described for the preparation of Compound A to yield a 1.94 g mixture of crude compounds A, C and D. A portion (0.95 g) of this mixture was separated by high speed countercurrent chromatography using the apparatus manufactured by P.C. Inc. (11805 Kim Place, Potomac, Md., U.S.A.) The crude mixture was concentrated in vacuo to dryness and dissolved in 4 mL of the upper phase and 4 mL of the lower phase of a solvent system consisting of 5 parts hexanes: 5 parts ethyl acetate: 5 parts methanol: 5 parts 0.1% aqueous $H_3PO_4$. The sample was applied to the tail of a #10 preparative multilayer coil (P.C. Inc.) which had been filled completely with the lower phase of the above solvent system. The coil was then eluted with the upper phase of the above solvent system from the tail of the column to the head of the column at 3.0 mL/min, at a rotation speed of 800 rpm in the forward direction. After collection of 156 fractions (7.5 mL each), the elution of the column with the upper phase was stopped and the stationary phase eluted in the reverse direction of flow (head- to-tail) at 9.0 mL/min collecting 1.0 min fractions to give fractions 1A-39A. Fractions were analyzed by RP HPLC as described in Example 1 Part B for the preparation of Compound A. Fractions 75 to 95 contained Compound C.

EXAMPLE 3

Preparation of Compound D

A. Culturing

Culture MF 5628 was grown according to the procedures of Example 1, Step A.

B. Isolation of Compound D

The isolation of Compound D was performed as described in Example 2. Fractions 120 to 160 of the high counter current separation contained 30 mg of crude Compound D. One half (15 mg) of this mixture was further purified by chromatography on a column Phenomenex Ultracarb 5 ODS 30, 15 cm×10 mm, eluted at 4.0 ml/min with a 1:1 mixture of solution A and B. Solution A was 0.1% $H_3PO_4$ in 400 ml acetonitrile and 600 ml water and solution B was 0.1% $H_3PO_4$ in 750 ml acetonitrile and 250 ml water. Fractions of 2 ml each were collected and numbers 24 to 27 were pooled, an equal volume of $H_2O$ added and the solution extracted with an equal volume of EtOAc. The EtOAc layer was concentrated to dryness in vacuo and contained 10.2 mg of Compound D.

EXAMPLE 4

Preparation of Compound F

A. Culturing MF5628

Culture MF5628 was grown according to the procedures of Example 1, Step A.

B. Isolation of Compound F

The isolation of Compound F was performed as described in Example 2. Fractions 28A-39A from the high speed countercurrent chromatography were pooled and extracted once with ethyl acetate. The ethyl acetate layer was dried over anhydrous $Na_2SO_4$ and concentrated to yield crude Compound F. A portion of this mixture separated by column chromatography on PHENOMENEX ULTRAGARB 5ODS 30 (10 mm×15 cm). The column was eluted at 3.0 mL/min. at 40° C. with 90% A/10% B from time 0 min. to 5 min. followed by a linear gradient to 100% B at time 40 min. (A=40% $CH_3CN$/60% $H_2O$/0.1% $H_3PO_4$, B=75% $CH_3CN$/25% $H_2O$/0.1% $H_3PO_4$) collecting 1.0 min. fractions. Fraction 29 was extracted once with 3 mL $CH_2Cl_2$ and the $CH_2Cl_2$ layer removed and concentrated to dryness to yield Compound F.

EXAMPLE 5

Preparation of Compound G

A. Culturing MF5628

Culture MF5628 was grown according to the procedures of Example 1, Step A.

B. Isolation of Compound G

The isolation of Compound G was performed as described above for Compound F. Fraction 32 was extracted once with 3 ml $CH_2Cl_2$ and the $CH_2Cl_2$ layer removed and concentrated to dryness to yield Compound G.

EXAMPLE 6

Preparation of Compound H

A. Culturing MF5628

Culture MF5628 was grown according to the procedures of Example 1, Step A.

B. Isolation of Compound H

The isolation of Compound H was performed as described above in Example 2. Fractions 51-61 from the high speed countercurrent chromatography were pooled and concentrated to dryness to yield crude Compound H. A portion (20 mg) of this mixture was further purified by column chromatography on PHENOMENEX ULTRACARB 5 ODS 30 (10 mm×15 cm). The sample was dissolved in 0.26 mL mobile phase and loaded onto the column. The column was eluted at 40° C. with a solution of 50% $CH_3CN$/50% $H_2O$/0.1% $H_3PO_4$ at 3.0 mL/min collecting 1.0 min. fractions. Fractions 6–7 were pooled and extracted once with an equal volume of ethyl acetate. The ethyl acetate layer was dried over anhydrous $Na_2SO_4$ and concentrated to dryness to yield Compound H.

EXAMPLE 7–14

Step A. Isolation of a Crude Mixture of Compounds A–T

A 9 day 4230 mL solid fermentation in BRF media (grown according to the procedures of Example 1, Step A) was extracted with 4230 mL methyl ethyl ketone (MEK) by stirring 1 hour. The MEK extract was collected by vacuum filtration and the solids extracted with an additional 3000 mL MEK. The second extract was collected by filtration, combined with the first extract and concentrated to dryness in vacuo to a greenish-brown syrup.

The concentrated extract from above was dissolved in 1500 mL of a solution of buffer 1 (800 mL water/1200 mL acetonitrile/4.28 mL concentrated formic acid and the pH adjusted 4.5 with a solution of 2.0 N NaOH). After complete dissolution the extract solution was adjusted to pH 4.5. This solution was then extracted twice with 1000 mL hexanes to yield a defatted extract (985 mL). A 940 mL portion of the defatted aqueous extract was then applied at a flow rate of 650 mL/hour to a column of BioRad AG4x4 (formate cycle, 5.0 cm×25 cm, 100–200 mesh) which had been prepared as follows: AG4x4 resin (free base form) was slurried in two volumes of a solution of 60 parts acetonitrile/40 parts water and the pH of the slurry adjusted to 4.5 with 2.0 N NaOH, the resin packed into a column of the above dimensions and then washed with 150 mL of buffer 1. After complete loading of the extract the column was washed with 300 mL buffer 1. The compounds were eluted from the resin with a solution of 1200 mL acetonitrile/800 mL water/11.2 mL concentrated sulfuric acid at a flow rate of 650 mL/hour and 150 mL fractions collected. Fractions 6–8 contained a mixture compounds A–T and were pooled (450 mL), 400 mL water added and the solution extracted with 800 mL of ethyl acetate. The ethyl acetate layer was removed, washed once with brine, dried over anhydrous $Na_2SO_4$ and concentrated in vacuo to a greenish-brown syrup.

Step B: Separation of Compounds A–T

The concentrated mixture of compounds A–T from above dissolved in ethyl acetate to a final volume of 50 mL. A 20 mL portion of this solution was concentrated to dryness in vacuo and separated by chromatography of a 5 cm×25 cm column of 12 micron Lichrospher 60 RP—select B (E. Merck). The column was equilbrated a 8 mL/min. with a mixture of 75% solution A (40 parts acetonitrile/60 parts water/0.1 part concentrated phosphoric acid):25% solution B (80 parts acetonitrile/20 parts water/0.1 part concentrated phosphoric acid). The 20 mL portion of the crude mixture of compounds A–T was dissolved in solution B to a final volume of 5 mL and applied to the column. The column was eluted with a gradient of solution A:solution B as follows:

| Time (min) | % A/% B | Flow Rate (ml/min) |
|---|---|---|
| 0 | 75/25 | 8 |
| 1 | 75/25 | 40 |
| 19 | 75/25 | 40 |
| 70 | 0/100 | 40 |

The column effluent was monitored at 220 run and 0.5 min (20 mL) fractions were collected.

Fractions were analyzed by RP HPLC on PHENOMENEX ULTRACARB 5 ODS 30, 15 cm×4.6 mm, flow rate 1.0 mL/min at 40° C., detection at 205 or 220 nm. Samples were dissolved 200 μg/mL in mobile phase and 20 μL injected. The following solvent systems were used:

| Solvent System | $CH_3CN$ | $H_2O$ | $H_3PO_4$ |
|---|---|---|---|
| A | 80% | 20% | 0.1% |
| B | 52% | 48% | 0.1% |
| C | 44% | 56% | 0.1% |

Relative retention times (RTT) were measured with respect to Compound A for solvent systems B and C and Compound E for solvent system A.

Fractions 20,22,24,26 and 32 were individually desalted by extraction with an equal volume of ethyl acetate, the ethyl acetate washed with brine and then dried over anhydrous $Na_2SO_4$. The ethyl acetate layer was concentrated to yield crude fraction 20 (4 mg), fraction 22 (3 mg), fraction 24 (3.5 mg), fraction 26 (2 mg) and fraction 32 (9 mg). The above fractions and the fraction pools described below were analyzed by HR-FAB MS to characterize the minor components present.

EXAMPLE 7

Isolation of Compound E

Fractions 108–110 from the above reverse phase chromatography were pooled (volume=140 mL), concentrated in vacuo to 41 mL and the solution extracted once with an equal volume of ethyl acetate. The ethyl acetate layer was washed once with brine, dried over anhydrous $Na_2SO_4$ and concentrated to dryness to yield Compound E.

EXAMPLE 8

Isolation of Compound C

Fractions 86–90 from the above reverse phase chromatography were pooled (volume=200 mL), concentrated in vacuo to 87 mL and the solution extracted once with an equal volume of ethyl acetate. The ethyl acetate layer was washed once with brine, dried over anhydrous $Na_2SO_4$ and concentrated to dryness to yield Compound C.

EXAMPLE 9

Isolation of Compound F and Q

Fractions 74–77 from the above reverse phase chromatography were pooled, worked up as described for the isolation of Compound C to yield 24 mg of a mixture containing Compounds F and Q.

EXAMPLE 10

Isolation of Compound S and R

Fractions 78-79 from the above reverse phase chromatography were pooled, worked up as described for the isolation of Compound C to yield 24 mg of a mixture containing Compounds J and K.

EXAMPLE 11

Isolation of Compounds L and T

Fractions 136-143 from the above reverse phase chromatography were pooled, worked up as described for the isolation of Compound C to yeild 9 mg of a mixture containing compounds L and T.

EXAMPLE 12

Isolation of Compound M

Fractions 111-119 from the above reverse phase chromatography were pooled, worked up as described for the isolation of Compound C to yield 19 mg of a mixture containing Compound M.

EXAMPLE 13

Isolation of Compound N

Fraction 48 from the above reverse phase chromatography was worked up as described for the isolation of Compound C to yield 54 mg of a mixture containing Compound N and Compound A.

EXAMPLE 14

Isolation of Compound O

Fraction 44 from the above reverse phase chromatography was worked up as described for the isolation of Compound C to yield 5 mg of a mixture containing Compound O.

EXAMPLE 15

Preparation of an Ammonium Salt

A 0.1 mmol sample of the free acid of a compound of formula (I) is dissolved in 10 mL ethyl acetate. The resulting solution is saturated with gaseous ammonia and the ammonium salt precipitates from solution.

EXAMPLE 16

Preparation of a Potassium Salt

A solution of 0.1 mmol of the free acid of a compound of formula (I) in 10 mL methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion, the sodium and lithium salts can be formed.

EXAMPLE 17

Preparation of a Calcium Salt

A solution of 0.1 mmol of the free acid of a compound of formula (I) in 20 mL 6:4 methanol:water is treated with an aqueous solution of 0.1 mmol of calcium hydroxide. The solvents are evaporated to give the corresponding calcium salt.

EXAMPLE 18

Preparation of an Ethylenediamine Salt

A solution of 0.1 mmol of the free acid of a compound of formula (I) in 10 mL of methanol is treated with 0.1 mmol of ethylenediamine. Evaporation of the solvent affords the ethylenediamine salt.

The procedure can also be applied to the preparation of the N,N"-dibenzylethylenediamine salt.

EXAMPLE 19

Preparation of a Tris(hydroxymethyl)aminomethane Salt

To a solution of 0.1 mmol of the free acid of a compound of formula (I) in 10 mL of methanol is added from 0.1 to 0.3 mmol of tris(hydroxymethyl)aminomethane dissolved in 10 mL methanol. Evaporation of the solvent gives a corresponding salt form, the exact composition of which is determined by the molar ratio of amine added. Similarly prepared are the salts of L-ornithine, L-lysine, and N-methylgluatamine.

EXAMPLE 20

Preparation of an L-arginine Salt

A solution of 0.1 mmol of the free acid of a compound of formula (I) in 20 mL of 6:4 methanol: water is treated with an aqueous solution of 0.1 to 0.3 mmol of L-arginine. Evaporation of the solvent affords the title salt, the exact composition of which is determined by the molar ratio of amino acid to the free acid of formula (I) used.

Similarly prepared are the salts of L-ornithine, L-lysine and N-methylglutamine.

EXAMPLE 21

Preparation of a Compound B (Method 1)

Compound A (0.6 mg) was dissolved in 1 mL diethyl ether and stirred at 0° C. Etheral cyanamide was added dropwise until the solution remained yellow. The solution was evaporated under a stream of nitrogen to yield Compound B.

Starting with Compounds C and D, the corresponding trimethyl esters may be prepared, following the procedures above.

EXAMPLE 22

Preparation of a Compound B (Method 2)

To 5 mg of Compound A in methanol (5 mL) was added 2 mL of freshly distilled diazomethane in ether (2.05M). After 5 minutes the solvent is removed to afford trimethyl ester (Compound B) as an oil.

Starting with Compounds C and D, the corresponding trimethyl esters may be prepared following the above procedure.

EXAMPLE 23

Preparation of Compound B (Method 3)

A solution of 5 mg of Compound A in 0.5 mL of tetrahydrofuran (THF) is treated at room temperature with 3 equivalents of N,N'-diisopropyl-O-benzyl isourea for 18 hours. The reaction mixture is then chilled to −15° C., filtered to remove the urea. The filtrate is concentrated under reduced pressure to yield Compound B.

This method is also suitable for the preparation of other ester derivatives such as: 1) methyl and the other lower alkyls, and 2) substituted benzyl esters, using the appropriately substituted isourea. By varying the number of equivalents of the substituted isourea used, the mono-, di- and tri-substituted esters may be selectively prepared. This method is also suitable for the preparation of mono, di and tri-substituted esters of Compounds C and D.

Mass Spectral Data

Mass spectra were recorded on Finnigan-MAT model MAT212 (Electron Impact, EI, 90 eV), TSQ70B (Fast Atom Bombardment, FAB, EI 70eV), and Jeol SX102 (EI, 90eV, FAB) mass spectrometers. Electron impact exact mass measurements were performed at high resolution (HR-EI) using perfluorokerosene (PFK) as internal standard. Fast Atom Bombardment (FAB) exact mass measurements were performed at high resolution (HR-FAB) useing polyethylene glycol (PEG)600 as internal standard.

$^{13}$C NMR Data $^{13}$C NMR spectra were recorded in $CD_3OD$ at 75 MHz on a Varian XL-300 spectrometer or at 100 MHz on a Varian Unity spectrometer. Chemical shifts are given in ppm relative to the solvent peak at 49.0 ppm ($CD_3OD$) as internal standard.

$^1$H NMR Spectra $^1$H NMR spectra were recorded at 300 MHz on a Varian XL-300 spectrometer and/or at 400 MHz or 500 MHz on a Varian Unity spectrometer. Chemical shifts are shown in ppm relative to the solvent peaks at 3.30 ppm ($CD_3OD$) as internal standards.

Physical Properties of the compounds of Structure I:

Compound A—the compound of structure (I) wherein $R_1$ is p-hydroxybenzyl, $R_2$ and $R_3$ together are oxo, $R_4$ is hydrogen, $R_5$ is $OZ_3$, $R_6$ is methyl, $R_7$ is $-N(R_4)CH(R_1)C(=O)OZ_1$, and $Z_1$, $Z_2$ and $Z_3$ are each hydrogen.

Mass Spectral Data: This compound has the molecular weight 591 by FAB MS (observed [M-H]$^-$ at m/z 590 and [M+H]$^+$ at m/z 592). The molecular formula was determined by exact mass measurement of the trimethyl ester (calc. for $C_{33}H_{45}NO_8$ 583.3145 M—($CH_3OH+H_2O$), found 583.3131).

$^1$H nmr (300 MHz, 18 mg in 0.7 ml $CD_3OD$):δ0.90 (t,7,3H), 1.29 (m, 14H), 1.53 (m, 4H), 1.98 (m, 2H), 2.44 (t, 7.2, 4H), 2.62 (d, 16.3, 1H), 2.89 (dd, 8.7, 13.3, 1H), 2.91 (d, 16.3, 1H), 3.11 (dd, 5.3, 14.3, 1H), 3.22 (d, 8.5, 1H), 4.61 (dd, 5.0, 8.7, 1H), 5.5 (m, 2H), 6.68 (d, 8.8, 2H), 7.03 (d, 8.8, 2H).

$^{13}$C nmr (75 MHz, 18 mg in 0.7 ml $CD_3OD$):δ14.42, 23.68, 24.83, 24.91, 29.83, 29.88, 30.06, 30.26, 30.29, 32.89, 33.46, 37.50, 43.10, 43.49 (2), 55.08, 57.77, 77.93, 116.21 (2), 124.52, 128.71, 131.38 (2), 137.56, 157.38, 173.55, 173.83, 174.48, 175.75, 214.62.

UV—(100 μg/ml in $CH_3OH$): 225 nm (8050), 277 nm (1420).

Compound B—the trimethyl ester of Compound A, i.e., the compound of structure (I) wherein $R_1$ is p-hydroxybenzyl, $R_2$ and $R_3$ together are oxo, $R_4$ is hydrogen, $R_5$ is $OZ_3$, $R_6$ is methyl, $R_7$ is $-N(R_4)CH(R_1)C(=O)OZ_1$, and $Z_1$, $Z_2$ and $Z_3$ are each methyl.

Mass Spectral Data: This compound has the molecular weight 633 by FAB-MS (observed [M+Li]$^+$ at m/z 640.)

$^1$ nmr (300 MHz, 0.6 mg in 0.7 ml $CD_3OD$):δ0.901 (t, 7.6) 1.295 (m), 1.536 (m), 1.992 (M), 2.439 (t, 7.3), 2.588 (d, 16.3), 2.865 (dd, 9.6, 14.3), 2.932 (d, 16.2), 3.073 (dd, 5.4, 14.2), 3.220 (d, 8.1), 3.641 (s), 3.709 (s), 3.716 (s), 4.610 (dd, 5.5, 8.7), 5.515 (m), 6.671 (d, 9.0), 6.988 (d, 8.1).

Compound C—the compound of structure (I) wherein $R_1$ is benzyl, $R_2$ and $R_3$ together are oxo, $R_4$ is hydrogen, $R_5$ is $OZ_3$, $R_6$ is methyl, $R_7$ is $-N(R_4)CH(R_1)C(=O)OZ_1$, and $Z_1$, $Z_2$ and $Z_3$ are each hydrogen.

Mass Spectral Data: This compound has the molecular weight of 575 by FAB-MS. (observed [M-H]$^-$ at m/z 574 and [M+H]$^+$ at m/z 576). HR-FAB indicated a molecular formula of $C_{31}H_{45}O_9N$ (found 576.3160, calculated 576.3172 for $C_{31}H_{46}O_9N$, [M+H]$_+$).

$^1$H nmr (300 MHz 6.2 mg in 0.5 mL $CD_3OD$):δ0.90 (t, 7, 3H), 1.29 (brm, 14H), 1.53 (m, 4H), 1.97 (m, 2H), 2.44 (t, 6.6, 4H), 2.56 (d, 16, 1H), 2.88 (d, 16, 1H), 2.98 (dd, 9.4, 14.3, 1H), 3.24 (5, 14.3 1H), 4.69 (dd, 4.9, 9.4, 1H), 5.54 (m, 2H), 7.24 (m, 5H).

$^{13}$C nmr (75 MHz, 6.2 mg in 0.5 mL $CD_3OD$):δ8 14.41, 23.67, 24.81, 24.92, 29.84, 29.88, 30.08, 30.25, 30.29, 32.89, 33.46, 38.24, 42.98, 43.48 (2), 54.81, 57.90, 77.90, 124.49, 127.88, 129.45 (2), 130.38 (2), 137.50, 138.18, 173.49, 173.79, 174.28, 175.63, 214.50.

Compound D—the compound of structure (I) wherein R is $-CH_2$—3-indolyl, $R_2$ and $R_3$ together are oxo, $R_4$ is hydrogen, $R_5$ is $OZ_3$, $R_6$ is methyl, $R_7$ is $-N(R_4)CH(R_1)C(=O)OZ_1$, and $Z_1$, $Z_2$ and $Z_3$ are each hydrogen.

Mass Specrtral Data: This compound has the molecular weight of 614 by FAB-MS (observed [M-H]$^-$ at m/z 613 and [M+H]$^+$ at m/z 615). HR-FAB indicates a molecular formula of $C_{33}H_{46}O_9N_2$ (found 615.3214, calculated 615.3281, for $C_{33}H_{47}O_9N_2$, [M+H]$^+$).

$^1$H nmr (300 MHz, 10.2 mg in 0.7 mL $CD_3OD$):δ0.90 (t, 6.3, 3H), 1.29 (m, 14H), 1.51 (m, 4H), 1.94 (m, 2H), 2.40 (t, 7.4, 2H), 2.42 (t, 7.4, 2H), 2.60 (d, 16.0, 1H), 2.90 (d, 16.0, 1H), 3.21 (d, 6.7, 1H), 3.22 (dd, 6.7, 14.5, 1H), 3.35 (dd, 4.9, 14.5, 1H), 4.76 (dd, 4.9, 8.0, 1H), 5.53 (m, 2H), 7.00 (ddd, 1.1, 7.0, 8.1, 1H), 7.06 (ddd, 1.1, 6.8, 8.6, 1H), 7.10 (s, 1H), 7.31 (dt, 1, 8.0, 1H), 7.56 (dt, 1, 7.8, 1H).

$^{13}$C nmr (75 MHz, 10.2 mg in 0.7 mL $CD_3OD$), δ 14.42, 23.68, 24.79, 24.90, 28.38, 29.76, 30.02, 30.25, 30.28, 32.89, 33.39, 43.06, 43.46, (2), 54.33, 57.74, 77.98, 110.63, 112.29, 119.33, 119.80, 122.39, 124.46, 124.69, 128.72, 137.68, 138.01, 173.49, 173.85, 174.85, 175.67, 214.59

UV (100 μg/mL in MeOH): 221 nm, 274 nm, 281 nm and 290 nm.

Compound E—The compound of structure (I) wherein $R_1$ is p-hydroxybenzyl, $R_2$ is H, $R_3$ is H, $R_4$ is H, $R_5$ is $OZ_3$, $R_6$ is methyl, $R_7$ is $-N(R_4)CB(R_1)C(=O)OZ_1$, and $Z_1$, $Z_2$ and $Z_3$ are each H.

Mass Spectral Data: This compound has the molecular weight of 577 by FAB-MS (observed [M-B]$^-$ at m/z 576 and [M+B]$^+$ at m/z 578). BR-FAB indicates a molecular formula of $C_{31}H_{47}O_9N$ (found 578.3304, calculated 578.3329, for $C_{31}H_{48}O_9N$, [M+B]$^+$).

$^1$H nmr (400 MHz, 10 mg in 0.7 mL $CD_3OD$): δ0.89 (t, 7.2, 3H), 1.27 (m, 24H), 1.97 (m, 2H), 2.61 (d, 16.4, 1H), 2.89 (dd, 8.8, 14.0 1B), 2.90 (d, 15.6, 1H), 3.10 (dd, 5.2, 14.4, 1H), 3.20 (d, 8.0, 1H), 4.60 (dd, 4.8, 8.8, 1H), 5.54 (m, 2H), 6.67 (d, 8.8, 2H), 7.01 (d, 8.8, 2H).

$^{13}$C nmr (100 MHz, 10 mg in 0.7 mL $CD_3OD$): δ14.45, 23.74, 30.16, 30.24, 30.48, 30.62, 30.77(6), 33.08, 33.61, 37.51, 43.07, 55.07, 57.83, 77.93, 116.20(2), 124.35, 128.67, 131.36(2), 137.73, 157.36, 173.48, 173.80, 174.43, 175.67.

Compound F—The compound of structure (I) wherein $R_1$ is 3-indolyl, $R_2$ is H, $R_3$ is OH, $R_4$ is H, $R_5$ is $OZ_3$, $R_6$ is methyl, $R_7$ is $-N(R_4)CH(R_1)C(=O)OZ_1$, and $Z_1$, $Z_2$ and $Z_3$ are each H.

Mass Spectra Data: This compound has the molecular weight of 616 by FAB-MS (observed [M-E]$^-$ at m/z 615 and [M+H]$^+$ at m/z 617). HR-FAB indicates a molecular formula of $C_{33}H_{48}O_9N_2$ (found 617.3362, calculated 617.3438, for $C_{33}H_9O_9N_2$, [M+B]$^+$).

$^1$H nmr (500 MHz, 2 mg in 0.7 mL CD$_3$OD): δ0.90 (t, 6.0, 3H), 1.30 (m, 12H), 1.41 (m, 2H), 1.53 (m, 2H), 1.93 (m, 2H), 2.57 (d, 16.2, 1H), 2.87 (d, 16.1, 1H), 3.19 (d, 8.2, 1H), 3.21 (dd, 7.5, 15.0, 1H), 3.33 (dd, 5.5, 15.0, 1H), 3.48 (m, 1H), 4.74 (dd, 4.9, 7.7, 1H), 5.53 (m, 2H), 6.99 (ddd, 1.1, 7.0, 8.1, 1H), 7.06 (ddd, 1.1, 6.8, 8.0, 1H), 7.10 (s, 1H), 7.30 (dt, 0.8, 8.1, 1H), 7.55 (dt, 1.0, 8.0).

UV (MeOH): 221 nm, 281 nm, 290 nm.

Compound G—The compound of structure (I) wherein $R_1$ is p-hydroxybenzyl, $R_2$ and $R_3$ together are oxo, $R_4$ is H, $R_5$ is $OZ_3$, $R_6$ is n-propyl, $R_7$ is $-N(R_4)CH(R_1)C(=O)OZ_1$, and $Z_1$, $Z_2$ and $Z_3$ are each H.

Mass Spectral Data: This compound has the molecular weight of 619 by FAB-MS (observed [M-H]$^-$ at m/z 618 and [M+H]$^+$ at m/z 620). HR-EI on the trimethyl ester indicates a molecular formula of $C_{33}H_{49}O_{10}N$ (found=625.3642, calculated=625.3614 for $C_{36}H_{51}O_8N$, $C_{33}H_{49}O_{10}N+3\times CH_2-H_2O-H_2O$).

$^1$H nmr (500 MHz, 1.0 mg in 0.7 mL CD$_3$OD): δ0.89 (t, 6.5, 3H), 1.28 (m, 18H), 1.52 (m, 4H), 1.98 (m, 2H), 2.42 (t, 7.5, 2H), 2.43 (t, 7.5, 2H), 2.59 (d, 16.0, 1H), 2.86 (d, 16.0, 1H), 2.90 (dd, 8.5, 14.0, 1H), 3.09 (dd, 5.0, 14.0, 1H), 3.20 (d, 8.5, 1H), 4.59 (dd, 5.0, 8.0, 1H), 5.54 (m, 2H), 6.66 (d, 9.0, 2H), 7.03 ( d, 9.0, 2H).

Compound H—The compound of structure (I) wherein $R_1$ is p-hydroxybenzyl, $R_2$ and $R_3$ together are oxo, $R_4$ and $R_5$ together are a single bond, $R_6$ is methyl, $R_7$ is $-N(R_4)CH(R_1)C(=O)OZ_1$, and $Z_1$, $Z_2$ and $Z_3$ are each hydrogen.

Mass Spectral Data: This compound has the molecular weight of 573 by FAB-MS (observed [M-H]$^-$ at m/z 572 and [M+H]$^+$ at m/z 574). HR-FAB indicates a molecular formula of $C_{31}H_{43}O_9N$ (found=574.3019, calculated=574.3015 for $C_{31}H_{44}O_9N$, [M+H]$^+$).

$^1$H nmr (300 MHz, 13.6 mg in 0.7 mL CD$_3$OD): δ0.90 (t, 6.5, 3H), 1.30 (m, 14H), 1.54 (m, 4H), 1.99 (m, 2H), 2.45 (t, 7.2, 4H), 2.57 (AB quartet, 2H), 3.18 (dd, 10.3, 14.3, 1H), 3.27 (d, 8.6, 1H), 3.37 (dd, 5.7, 14.3 1H), ~4.9 (obscured under HDO peak, 1H), 5.15 (ddt, 1.3, 8.8, 15.5, 1H), 5.70 (dt, 7.0, 15.3, 1H), 6.66 (d, 8.5, 2H), 6.98 (d, 8.4, 2H).

$^{13}$C nmr (75 MHz, 13.6 mg in 0.7 mL CD$_3$OD): δ 14.22, 23.68, 24.81, 24.92, 29.71, 29.87, 30.02, 30.25, 30.29, 32.89, 33.56, 34.28, 38.86, 43.44, 43.50, 55.24, 57.13, 76.87, 116.23 (2), 121.43, 129.24, 131.26 (2), 140.62, 157.30, 171.60, 173.16, 176.93, 178.44, 214.52.

The characterization of the Compounds isolated in Examples 7 through 14 are detailed in Table 2 which follows:

TABLE 2

| Fraction | Mwt | Formula | Found [M + H]$^+$ | Calculated | For | RRT/Solvent System | Structure |
|---|---|---|---|---|---|---|---|
| 20 | 607 | $C_{31}H_{45}NO_{11}$ | 608.3105 | 608.3070 | $C_{31}H_{46}NO_{11}$ | — | — |
|  | 589 | $C_{31}H_{43}NO_{10}$ | 590.3049 | 590.2964 | $C_{31}H_{44}NO_{10}$ | — | — |
|  | 609 | $C_{31}H_{47}NO_{11}$ | 610.3225 | 610.3227 | $C_{31}H_{48}NO_{11}$ | — | — |
|  | 573 | $C_{31}H_{43}NO_9$ | 574.3038 | 574.3015 | $C_{31}H_{44}NO_9$ | — | — |
| 22 | 589 | $C_{31}H_{43}NO_{10}$ | 590.3018 | 590.2964 | $C_{31}H_{44}NO_{10}$ | — | — |
|  | 609 | $C_{31}H_{47}NO_{11}$ | 610.3259 | 610.3227 | $C_{31}H_{48}NO_{11}$ | — | — |
|  | 573 | $C_{31}H_{43}NO_9$ | 574.3049 | 574.3015 | $C_{31}H_{44}NO_9$ | — | — |
| 24 | 589 | $C_{31}H_{43}NO_{10}$ | 590.2986 | 590.2964 | $C_{31}H_{44}NO_{10}$ | — | Cmpd. P |
|  | 609 | $C_{31}H_{47}NO_{11}$ | 610.3176 | 610.3227 | $C_{31}H_{48}NO_{11}$ | — | — |
|  | 607 | $C_{31}H_{45}NO_{11}$ | 608.3024 | 608.3070 | $C_{31}H_{46}NO_{11}$ | — | — |
|  | 605 | $C_{31}H_{43}NO_{11}$ | 606.2904 | 606.2914 | $C_{31}H_{44}NO_{11}$ | — | — |
|  | 573 | $C_{31}H_{43}NO_9$ | 574.3049 | 574.3015 | $C_{31}H_{44}NO_9$ | — | — |
| 26 | 609 | $C_{31}H_{47}NO_{11}$ | 610.3176 | 610.3227 | $C_{31}H_{48}NO_{11}$ | — | — |
|  | 607 | $C_{31}H_{45}NO_{11}$ | 608.3058 | 608.3070 | $C_{31}H_{46}NO_{11}$ | — | — |
|  | 605 | $C_{31}H_{43}NO_{11}$ | 606.2904 | 606.2914 | $C_{31}H_{44}NO_{11}$ | — | — |
|  | 589 | $C_{31}H_{43}NO_{10}$ | 590.2988 | 590.2964 | $C_{31}H_{44}NO_{10}$ | — | — |
|  | 573 | $C_{31}H_{43}NO_9$ | 574.3011 | 574.3015 | $C_{31}H_{44}NO_9$ | — | — |
| 32 | 607 | $C_{31}H_{45}NO_{11}$ | 608.3044 | 608.3070 | $C_{31}H_{46}NO_{11}$ | — | — |
|  | 605 | $C_{31}H_{43}NO_{11}$ | 606.2858 | 606.2914 | $C_{31}H_{44}NO_{11}$ | — | — |
|  | 589 | $C_{31}H_{43}NO_{10}$ | 590.2988 | 590.2987 | $C_{31}H_{44}NO_{10}$ | — | — |
|  | 567 | $C_{29}H_{45}NO_{10}$ | 568.3093 | 568.3121 | $C_{29}H_{46}NO_{10}$ | — | — |
|  | 565 | $C_{29}H_{43}NO_{10}$ | 566.2981 | 566.2964 | $C_{29}H_{44}NO_{10}$ | — | — |
| 44 | 577 | $C_{30}H_{43}NO_{10}$ | 578.2999 | 578.2965 | $C_{30}H_{44}NO_{10}$ | 0.58/C | Cmpd. O |
|  | 593 | $C_{31}H_{47}NO_{10}$ | 594.3224 | 594.3278 | $C_{31}H_{48}NO_{10}$ | — | — |
| 48 | 593 | $C_{31}H_{47}NO_{10}$ | 594.3279 | 594.3278 | $C_{31}H_{48}NO_{10}$ | 0.82/C | Cmpd. N |
| 50–64 | 591 |  |  |  |  | 1.0/B,C | Cmpd. A |
| 65–73 | 630 | $C_{33}H_{46}N_2O_{10}$ | 631.3188 | 631.3230 | $C_{33}H_{47}N_2O_{10}$ | — | — |
| 74–77 | 616 | $C_{33}H_{48}N_2O_9$ | 617.3362 | 617.3438 | $C_{33}H_{49}N_2O_9$ | 1.80/B | Cmpd. F |
|  | 559 | $C_{31}H_{45}NO_8$ | 560.3193 | 560.3223 | $C_{31}H_{46}NO_8$ | 1.67/B | Cmpd. Q |
| 78–79 | 577 | $C_{31}H_{47}NO_9$ | 578.3313 | 578.3329 | $C_{31}H_{48}NO_9$ | 2.16/B | Cmpd. S |
|  | 561 | $C_{30}H_{43}NO_9$ | 562.3058 | 562.3016 | $C_{30}H_{44}NO_9$ | 1.90/B | Cmpd. R |
| 80–83 | 614 | $C_{33}H_{46}N_2O_9$ | 615.3214 | 615.3281 | $C_{33}H_{47}N_2O_9$ | 2.21/B | Cmpd. D |
| 86–90 | 575 | $C_{31}H_{45}NO_9$ | 576.3160 | 576.3172 | $C_{31}H_{46}NO_9$ | 2.66/B | Cmpd. C |
| 108–110 | 577 | $C_{31}H_{47}NO_9$ | 578.3304 | 578.3329 | $C_{31}H_{48}NO_9$ | 4.56/B | Cmpd. E |
| 111–119 | 603 | $C_{33}H_{49}NO_9$ | 604.3450 | 604.3485 | $C_{33}H_{50}NO_9$ | — | Cmpd. M |
|  | 579 | $C_{27}H_{49}NO_{12}$ | 580.3333 | 580.3332 | $C_{27}H_{50}NO_{12}$ | — | — |
|  | 577 | $C_{27}H_{47}NO_{12}$ | 578.3213 | 578.3176 | $C_{27}H_{48}NO_{12}$ | — | — |
| 136–143 | 561 | $C_{31}H_{47}NO_8$ | 562.3354 | 562.3379 | $C_{31}H_{48}NO_8$ | — | Cmpd. L |
|  | 428 | $C_{23}H_{40}O_7$ | 429.2863 | 429.2852 | $C_{23}H_{41}O_7$ | — | Cmpd. T |

What is claimed is:

1. A compound of structural formula (I)

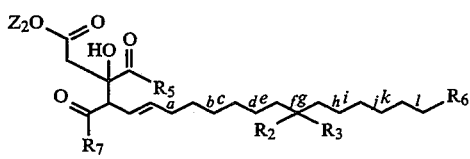

wherein
R₁ is

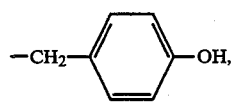
(a)

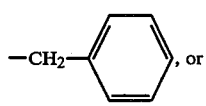
(b)

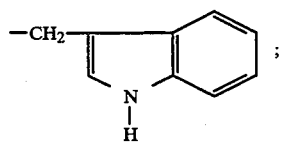
(c)

R₂ and R₃ are each H, or R₂ is H and R₃ is OH, or R₂ and R₃ together are oxo;

R₄ is H and R₅ is OZ₃, or R₄ and R₅ are a single bond forming a 2,5-dioxopyzrolidine;

R₆ is (a) hydrogen, or (b) $C_{1-3}$ alkyl;

R₇ is: (a) —OZ₁, or

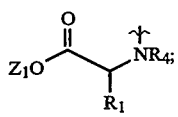
(b)

each of a, b, c, d, e, f, g, h, i, j, k, and l are a single bond or one of a, b, c, d, e, f, g, h, i, j, k, and l is a double bond, provided that when f or g is a double bond, R₂ is absent and R₃ is H; and Z₁, Z₂ and Z₃ are each independently
 a) H,
 b) $C_{1-5}$ alkyl, or
 c) $C_{1-5}$ alkyl substituted with
   i) phenyl, or
   ii) phenyl substituted with methyl, methoxy, Cl, Br, I, F or hydroxy;
or a pharmaceutically acceptable salt of a compound of formula (I).

2. The compound of claim 1 in which R₇ is —N(R₄)CH(R₁)C(=O)OZ₁, and Z₁, Z₂ and Z₃ are each hydrogen or a pharmaceutically acceptable mono, di or tri salt thereof.

3. The compound of claim 1 in which Z₁, Z₂ and Z₃ are each methyl.

4. The compound of claim 1 of structural formula (II):

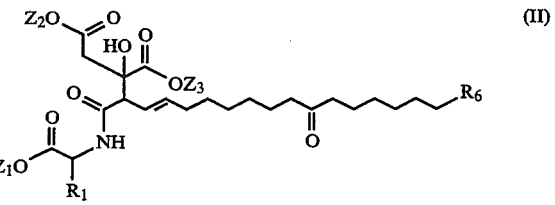

wherein R₁, R₆, Z₁, Z₂ and Z₃ are:

| | R₁ | R₆ | Z₁ | Z₂ | Z₃ |
|---|---|---|---|---|---|
| (a) | p-hydroxybenzyl | methyl | H | H | H |
| (b) | p-hydroxybenzyl | methyl | H | methyl | H |
| (c) | p-hydroxybenzyl | methyl | methyl | H | H |
| (d) | p-hydroxybenzyl | methyl | methyl | methyl | H |
| (e) | p-hydroxybenzyl | methyl | methyl | methyl | methyl |
| (f) | benzyl | methyl | H | H | H |
| (g) | 3-indolyl | methyl | H | H | H |
| (h) | p-hydroxybenzyl | n-propyl | H | H | H |
| (i) | benzyl | hydrogen | H | H | H |
| (j) | benzyl | propyl | H | H | H |
| (k) | p-hydroxybenzyl | hydrogen | H | H | H. |

5. The compound of claim 1 of structural formula (III):

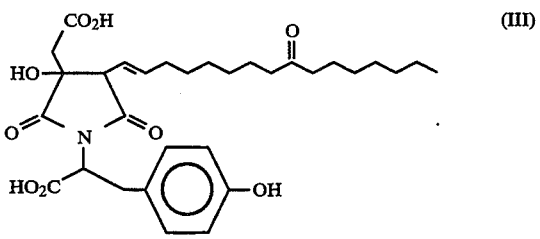

6. The compound of claim 1 of structural formula (IV):

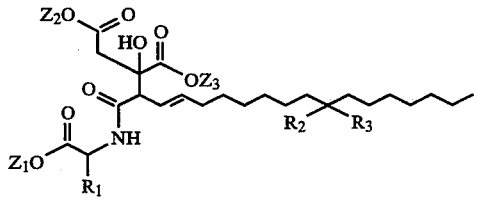

wherein R₁, R₂, R₃, Z₁, Z₂ and Z₃ are:

| | R₁ | R₂ | R₃ | Z₁ | Z₂ | Z₃ |
|---|---|---|---|---|---|---|
| (a) | 3-indolyl | H | OH | H | H | H |
| (b) | p-hydroxybenzyl | H | H | H | H | H |
| (c) | benzyl | H | OH | H | H | H |
| (d) | benzyl | H | H | H | H | H. |

7. The compound according to claim 1 wherein Z₁ is OH, Z₂ is OH, Z₃ is OH, R₄ is H, R₅ is OH, R₇ is —N(R₄)CH(R₁)C(=O)OZ₁ and R₁, R₂, R₃, and R₆ are as below:

| | R₁ | R₂ | R₃ | R₆ |
|---|---|---|---|---|
| (a) | benzyl | —H | —H | —CH₃ |
| (b) | benzyl | oxo with R₃ | oxo with R₂ | —CH₂CH₂CH₃ |
| (c) | p-hydroxybenzyl | —H | —OH | —CH₃ |

-continued

| $R_1$ | $R_2$ | $R_3$ | $R_6$ |
|---|---|---|---|
| (d) p-hydroxybenzyl | oxo with $R_3$ | oxo with $R_2$ | —H |
| (e) benzyl | oxo with $R_3$ | oxo with $R_2$ | —H |
| (f) benzyl | —H | —OH | —CH$_3$. |

8. The compound of claim 1 wherein $R_7$ is —N(R$_4$)CH(R$_1$)C(=O)OZ$_1$, R$_4$ is hydrogen, R$_5$ is OZ$_3$, Z$_1$, Z$_2$ and Z$_3$ are each hydrogen, and one of a, b, c, d, e, f, g, h, i, j, k, and l is a double bond provided that when f or g is a double bond, and R$_1$, R$_2$, R$_3$, and R$_6$ are as shown in the table below:

| $R_1$ | $R_2$ | $R_3$ | $R_6$ |
|---|---|---|---|
| (a) benzyl | H | H | methyl |
| (b) p-hydroxybenzyl | oxo with $R_3$ | oxo with $R_2$ | methyl. |

9. The compound of claim 1 wherein $R_7$ is —OZ$_1$.

10. The compound according to claim 1 selected from:

(a)
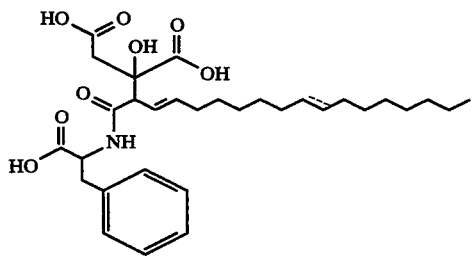

(b)
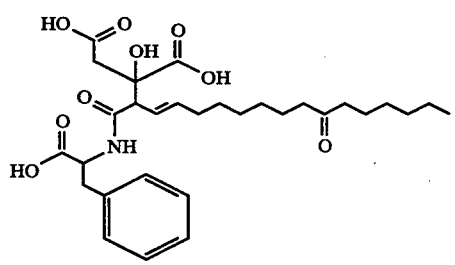

(c)
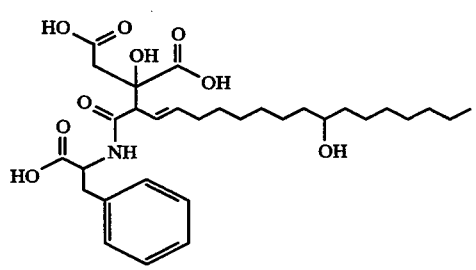

(d)
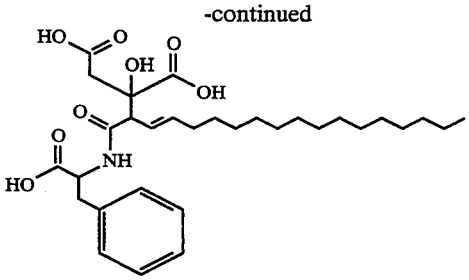

(e)
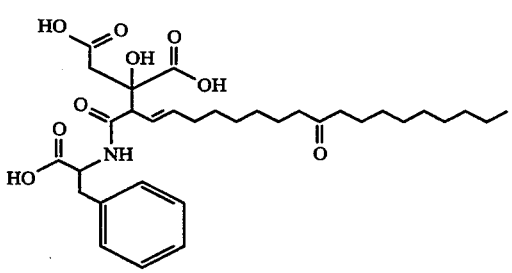

(f)
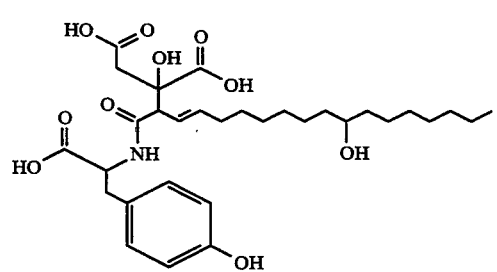

(g)
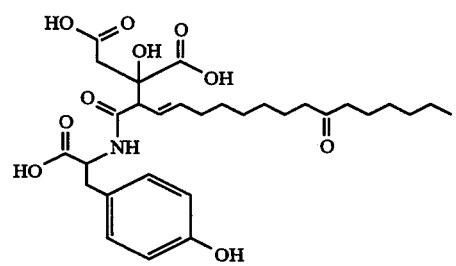

(h)
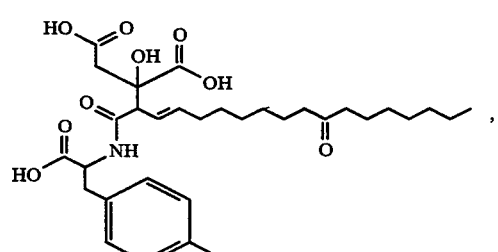

and (i)
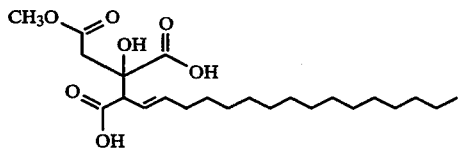

wherein: the dashed line indicates the presence of a double bond along the alkenyl chain.

11. A pharmaceutical composition comprising a nontoxic therapeutically effective amount of a compound of claim 1 and a pharmaceutically acceptable carrier.

* * * * *